US012751648B2

(12) United States Patent
Patek et al.

(10) Patent No.: US 12,751,648 B2
(45) Date of Patent: Oct. 6, 2026

(54) SYSTEM, METHOD, AND COMPUTER READABLE MEDIUM FOR A BASAL RATE PROFILE ADAPTATION ALGORITHM FOR CLOSED-LOOP ARTIFICIAL PANCREAS SYSTEMS

(71) Applicant: UNIVERSITY OF VIRGINIA PATENT FOUNDATION, Charlottesville, VA (US)

(72) Inventors: Stephen D. Patek, Charlottesville, VA (US); Jonathan Hughes, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 22 days.

(21) Appl. No.: 16/486,049

(22) PCT Filed: Feb. 15, 2018

(86) PCT No.: PCT/US2018/018414
§ 371 (c)(1),
(2) Date: Aug. 14, 2019

(87) PCT Pub. No.: WO2018/152358
PCT Pub. Date: Aug. 23, 2018

(65) Prior Publication Data

US 2020/0046268 A1 Feb. 13, 2020

Related U.S. Application Data

(60) Provisional application No. 62/459,100, filed on Feb. 15, 2017.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0022* (2013.01); *A61B 5/4839* (2013.01);
(Continued)

(58) Field of Classification Search
CPC . A61B 5/14532; A61B 5/0022; A61B 5/4839; A61B 5/7275; A61M 5/142;
(Continued)

(56) References Cited

U.S. PATENT DOCUMENTS

| | | | |
|---|---|---|---|
| 6,923,763 | B1 | 8/2005 | Kovatchev et al. |
| 7,025,425 | B2 | 4/2006 | Kovatchev et al. |

(Continued)

FOREIGN PATENT DOCUMENTS

| | | | |
|---|---|---|---|
| CN | 103418053 | A | 12/2013 |
| JP | 2010524639 | A | 7/2010 |

(Continued)

OTHER PUBLICATIONS

The extended European Search Report issued on Nov. 11, 2020, by the European Patent Office in corresponding European Application No. 18754079.4. (8 pages).

(Continued)

*Primary Examiner* — Jason M Sims
*Assistant Examiner* — Kyle W. Kretzer
(74) *Attorney, Agent, or Firm* — Buchanan Ingersoll & Roone .P.C

(57) ABSTRACT

An insulin device configured to control insulin dosage adapts a basal rate profile, using a sensor configured to produce a blood glucose level measurement data, and detect changes of the blood glucose level measurement data over time. A processor is configured to receive the blood glucose level measurement data and a basal rate profile. A basal rate set point corresponds to an insulin delivery reference for a nominal blood glucose. The insulin device includes an (Continued)

insulin dispensing valve controlled by the processor to administer insulin in accordance with the received basal rate profile. The processor is configured to update the basal rate set point over a time period based on both an assessment of at least one of a risk of hyperglycemia and a risk of hypoglycemia from historical blood glucose data, and patterns of actions taken by the insulin device to mitigate glycemic risk during the time period.

15 Claims, 6 Drawing Sheets

(51) Int. Cl.
*A61M 5/142* (2006.01)
*A61M 5/172* (2006.01)
*G16H 20/17* (2018.01)
*G16H 50/30* (2018.01)
*A61M 5/14* (2006.01)
*G16H 40/63* (2018.01)

(52) U.S. Cl.
CPC ........... *A61B 5/7275* (2013.01); *A61M 5/142* (2013.01); *A61M 5/1723* (2013.01); *G16H 20/17* (2018.01); *G16H 50/30* (2018.01); *A61M 5/14* (2013.01); *A61M 5/172* (2013.01); *G16H 40/63* (2018.01)

(58) Field of Classification Search
CPC ...... A61M 5/1723; A61M 5/14; A61M 5/172; G16H 40/63; G16H 20/17; G16H 50/30
See application file for complete search history.

(56) References Cited

U.S. PATENT DOCUMENTS

| | | | | |
|---|---|---|---|---|
| 7,815,569 | B2 | 10/2010 | Kovatchev et al. | |
| 7,874,985 | B2 | 1/2011 | Kovatchev et al. | |
| 7,972,296 | B2 | 7/2011 | Braig et al. | |
| 8,135,548 | B2 | 3/2012 | Breton et al. | |
| 8,449,524 | B2 | 5/2013 | Braig et al. | |
| 8,562,587 | B2 | 10/2013 | Kovatchev et al. | |
| 8,585,593 | B2 | 11/2013 | Kovatchev et al. | |
| 8,718,958 | B2 | 5/2014 | Breton et al. | |
| 9,317,657 | B2 | 4/2016 | Breton et al. | |
| 9,398,869 | B2 | 7/2016 | Kovatchev et al. | |
| 9,414,782 | B2 | 8/2016 | Braig et al. | |
| 9,430,022 | B2 | 8/2016 | Kovachev et al. | |
| 2005/0214892 | A1 | 9/2005 | Kovatchev et al. | |
| 2007/0016127 | A1* | 1/2007 | Staib | A61B 5/14532 604/504 |
| 2008/0154513 | A1 | 6/2008 | Kovatchev et al. | |
| 2008/0269714 | A1 | 10/2008 | Mastrototaro et al. | |
| 2008/0269723 | A1 | 10/2008 | Mastrototaro et al. | |
| 2008/0314395 | A1 | 12/2008 | Kovatchev et al. | |
| 2009/0131861 | A1 | 5/2009 | Braig et al. | |
| 2009/0171589 | A1 | 7/2009 | Kovatchev | |
| 2010/0174266 | A1* | 7/2010 | Estes | G16H 20/17 604/504 |
| 2010/0179768 | A1 | 7/2010 | Kovatchev et al. | |
| 2010/0198520 | A1 | 8/2010 | Breton et al. | |
| 2010/0249561 | A1 | 9/2010 | Patek et al. | |
| 2011/0264071 | A1 | 10/2011 | Braig et al. | |
| 2011/0313351 | A1 | 12/2011 | Kamen et al. | |
| 2012/0004512 | A1 | 1/2012 | Kovatchev et al. | |
| 2012/0078067 | A1 | 3/2012 | Kovatchev et al. | |
| 2012/0130698 | A1 | 5/2012 | Kovatchev et al. | |
| 2012/0136336 | A1 | 5/2012 | Mastrototaro et al. | |
| 2012/0191361 | A1 | 7/2012 | Kovatchev et al. | |
| 2012/0245556 | A1 | 9/2012 | Kovatchev et al. | |
| 2012/0246106 | A1* | 9/2012 | Atlas | G16H 50/20 700/282 |
| 2013/0116649 | A1 | 5/2013 | Breton et al. | |
| 2013/0165900 | A1 | 6/2013 | Braig et al. | |
| 2014/0012511 | A1* | 1/2014 | Mensinger | G16H 20/17 702/19 |
| 2014/0039383 | A1* | 2/2014 | Dobbles | A61M 15/0068 604/66 |
| 2014/0046159 | A1 | 2/2014 | Kovatchev et al. | |
| 2014/0244216 | A1 | 8/2014 | Breton et al. | |
| 2015/0018633 | A1 | 1/2015 | Kovachev et al. | |
| 2015/0025495 | A1 | 1/2015 | Peyser | |
| 2015/0190098 | A1 | 7/2015 | Patek et al. | |
| 2015/0193589 | A1 | 7/2015 | Ortiz et al. | |
| 2015/0273147 | A1* | 10/2015 | Duke | A61B 5/14532 703/2 |
| 2016/0004813 | A1 | 1/2016 | Kovatchev et al. | |
| 2016/0007890 | A1 | 1/2016 | Kovatchev et al. | |
| 2016/0171183 | A1 | 6/2016 | Breton et al. | |
| 2016/0317744 | A1* | 11/2016 | Rule | A61B 5/14532 |
| 2016/0331310 | A1 | 11/2016 | Kovatchev | |
| 2017/0056591 | A1 | 3/2017 | Breton et al. | |
| 2017/0188943 | A1 | 7/2017 | Braig et al. | |
| 2018/0055452 | A1 | 3/2018 | Breton | |
| 2021/0186417 | A1 | 6/2021 | Braig et al. | |

FOREIGN PATENT DOCUMENTS

| | | | | |
|---|---|---|---|---|
| JP | 2011501681 | A | 1/2011 | |
| WO | 0113786 | A1 | 3/2001 | |
| WO | 0172208 | A2 | 10/2001 | |
| WO | 2004015539 | A2 | 2/2004 | |
| WO | 2005106017 | A2 | 11/2005 | |
| WO | 2007027691 | A1 | 3/2007 | |
| WO | 2007081853 | A2 | 7/2007 | |
| WO | 2008052199 | A2 | 5/2008 | |
| WO | 2008067284 | A2 | 6/2008 | |
| WO | 2008157780 | A1 | 12/2008 | |
| WO | 2008157781 | A1 | 12/2008 | |
| WO | 2009009528 | A2 | 1/2009 | |
| WO | 2010062898 | A1 | 6/2010 | |
| WO | 2010099313 | A1 | 9/2010 | |
| WO | 2010138848 | A1 | 12/2010 | |
| WO | 2010151834 | A1 | 12/2010 | |
| WO | 2011028731 | A1 | 3/2011 | |
| WO | 2011028925 | A1 | 3/2011 | |
| WO | 2011031351 | A1 | 3/2011 | |
| WO | 2011112974 | A1 | 9/2011 | |
| WO | 2011119832 | A1 | 9/2011 | |
| WO | 2012178113 | A1 | 12/2012 | |
| WO | 2012178134 | A2 | 12/2012 | |
| WO | 2013032965 | A1 | 3/2013 | |
| WO | 2013177565 | A1 | 11/2013 | |
| WO | 2014022864 | A1 | 2/2014 | |
| WO | 2014130841 | A1 | 8/2014 | |
| WO | 2015003124 | A2 | 1/2015 | |
| WO | 2015103543 | A1 | 7/2015 | |
| WO | 2016025874 | A1 | 2/2016 | |
| WO | WO-2016133879 | A1 * | 8/2016 | A61B 5/14532 |
| WO | 2016200970 | A1 | 12/2016 | |
| WO | 2016201120 | A1 | 12/2016 | |
| WO | 2017040927 | A1 | 3/2017 | |
| WO | 2017058927 | A1 | 4/2017 | |
| WO | 2017070553 | A1 | 4/2017 | |
| WO | 2017132663 | A1 | 8/2017 | |

OTHER PUBLICATIONS

C. Toffanin, et al., "Automatic Adaptation of Basal Therapy for Type 1 Diabetic Patients: A Run-to-Run Approach", Proceedings of the 19th World Congress, The International Federation of Automatic Control (IFAC), Cape Town, South Africa, Aug. 24-29, 2014, pp. 2070-2075.

Cobelli, et al., "Artificial Pancreas: Past, Present, Future", Diabetes, 2011, vol. 60(11), pp. 2672-2682.

Dalla Man, et al., "The UVA/PADOVA Type 1 Diabetes Simulator: New Features", Journal of Diabetes Science and Technology, 2014, vol. 8(1), pp. 26-34.

(56) References Cited

OTHER PUBLICATIONS

Del Favero, et al., "First Use of Model Predictive Control in Outpatient Wearable Artificial Pancreas", Diabetes Care, May 2014, vol. 37, No. 5, pp. 1212-1215.
Doyle, et al., "Closed-loop artificial pancreas systems: Engineering the algorithms", Diabetes Care, May 2014, vol. 37, No. 5, pp. 1191-1197.
Forlenza, et al., "Progress in Diabetes Technology: Developments in Insulin Pumps, Continuous Glucose Monitors, and Progress towards the Artificial Pancreas", The Journal of Pediatrics, Feb. 2016, vol. 169, pp. 13-20.
Gondhalekar, et al., Periodic zone-MPC with asymmetric costs for outpatient-ready safety of an artificial pancreas to treat type 1 diabetes, Automatica, Sep. 2016, vol. 71, pp. 237-246.
International Search Report (PCT/ISA/210) and Written Opinion (PCT/ISA/237) mailed on Apr. 23, 2018, by the U.S. Patent Office as the International Searching Authority for International Application No. PCT/US2018/018414.
Kovatchev, et al., "Evaluation of a New Measure of Blood Glucose Variability in Diabetes", Diabetes Care, Nov. 2006, vol. 29(11), pp. 2433-2438.
Kovatchev, et al., "Statistical Tools to Analyze Continuous Glucose Monitor Data", Diabetes Technology & Therapeutics, May 2009, vol. 11, pp. S45-S54.
Kovatchev, et al., "The Artificial Pancreas in 2016: A Digital Treatment Ecosystem for Diabetes", Diabetes Care, 2016 vol. 39, pp. 1123-1126.
Laimer, et al., "Variability of basal rate profiles in insulin pump therapy and association with complications in type 1 diabetes mellitus", PLoS One, Mar. 2016, vol. 11(3), pp. 1-10.
Owens, et al., "Run-to-Run Control of Blood Glucose Concentrations for People With Type 1 Diabetes Mellitus", IEEE Transactions on Biomedical Engineering, Jun. 2006, vol. 53, No. 6, pp. 996-1005.
Palerm, et al., "A Run-to-Run Control Strategy to Adjust Basal Insulin Infusion Rates in Type 1 Diabetes", Journal of Process Control, 2008, vol. 18(3), pp. 258-265.
Peyser, et al., "The artificial pancreas: current status and future prospects in the management of diabetes", Annals of the New York Academy of Sciences, 2014, vol. 1311, pp. 102-123.
Pinsker, et al., "Randomized Crossover Comparison of Personalized MPC and PID Control Algorithms for the Artificial Pancreas", Diabetes Care, Jul. 2016, vol. 39, pp. 1135-1142.
Thabit, et al., "Coming of age: the artificial pancreas for type 1 diabetes", Diabetologia, 2016, vol. 59, pp. 1795-1805.
Office Action (Notice of Reasons for Refusal) issued on Nov. 1, 2021, by the Japanese Patent Office in corresponding Japanese Patent Application No. 2019-545370, and an English Translation of the Office Action. (7 pages).
Office Action (Examination Report No. 1) issued on Oct. 4, 2022, by the Australian Patent Office in corresponding Australian Patent Application No. 2018221048. (3 pages).
Office Action (Notice of Reasons for Refusal) issued on Sep. 26, 2022, by the Japanese Patent Office in corresponding Japanese Patent Application No. 2019-545370, and an English Translation of the Office Action. (8 pages).
Office Action (Communication pursuant to Article 94(3) EPC) issued Sep. 27, 2023, by the European Patent Office in corresponding European Patent Application No. 18 754 079.4-1126. (6 pages).
Office Action (Examination Report No. 2) issued on Jul. 5, 2023, by the Australian Patent Office in corresponding Australian Patent Application No. 2018221048. (3 pages).
Office Action (Notification of Ground(s) for Refusal issued on Jun. 26, 2023, by the Japanese Patent Office in corresponding Japanese Patent Application No. 2019-545370, and an English Translation of the Office Action. (5 pages).
Office Action issued on Apr. 24, 2024, by the Canadian Patent Office in corresponding Canadian Patent Application No. 3,053,502. (4 pages).
Office Action (Examination Report No. 1) issued on Jan. 9, 2025, by the Australian Patent Office in corresponding Australian Patent Application No. 2023266248. (4 pages).
Office Action (Notice of Reasons for Refusal) issued on Jun. 12, 2025, by the Japanese Patent Office in corresponding Japanese Patent Application No. 2019-545370, and an English Translation of the Office Action. (7 pages).
Office Action issued on Jul. 16, 2025, by the Canadian Patent Office in corresponding Canadian Patent Application No. 3,053,502. (3 pages).
Office Action (Notice of Acceptance) issued on Dec. 11, 2025, by the Australian Patent Office in corresponding Australian Patent Application No. 2023266248. (3 pages).

* cited by examiner

SYSTEM, METHOD, AND COMPUTER READABLE MEDIUM FOR A BASAL RATE PROFILE ADAPTATION ALGORITHM FOR CLOSED-LOOP ARTIFICIAL PANCREAS SYSTEMS

RELATED APPLICATION

This application claims the benefit under 35 U.S.C. § 119 of U.S. Provisional Patent No. 62/459,100 filed on Feb. 15, 2017, the entire contents of which is hereby incorporated by reference in its entirety.

STATEMENT REGARDING FEDERALLY SPONSORED RESEARCH OR DEVELOPMENT

This disclosure was made with government support under Grant No. DK106826 awarded by the National Institutes of Health. The U.S. government has certain rights in the disclosure.

FIELD

An aspect of an embodiment of the present disclosure provides, among other features, a system, method, and computer readable medium to control an insulin dosage by adapting a basal rate profile.

BACKGROUND INFORMATION

Closed-loop control of insulin delivery for type-1 diabetic patients, commonly termed the AP or "artificial pancreas", is rapidly advancing. Recent advances in technology have made the use of closed-loop control systems for the management of insulin delivery for patients with type-1 diabetes—termed the "Artificial Pancreas" or "AP"—increasingly feasible (see documents "[1]" Kovatchev et al, "[2]" Thabit et al, and "[3]" Forlenza et al). Competing methodologies for the core control algorithms governing the AP, such as those based on model predictive control (MPC), proportional-integral-derivative (PID), or "fuzzy logic" based controllers, are all being developed, compared, and tested as potential centerpieces for a clinically implementable artificial pancreas (see documents "[4]" Peyser et al, "[5]" Pinsker et al, "[6]" Favero et al, and "[7]" Doyle et al). These procedures generally build upon the established insulin-pump therapy paradigm used for the control of type-1 diabetes. Thus, the algorithms take into account traditional treatment parameters for diabetes management such as "carbohydrate ratio", "basal insulin delivery rate", and "correction factor", to determine the insulin infusions delivered by the system during closed-loop control. These parameters, together with user input and sensor data, determine the actions that the AP will take to respond both to the actually realized and potentially (depending on the controller) even to projected variations in patient's blood glucose levels. Just as in more traditional therapies, these parameters should be individualized in order to maximize the effectiveness of treatment and account for inter-subject variability in response.

The following patents, applications and publications as listed below and throughout this document are hereby incorporated by reference in their entirety herein.

[1] Boris Kovatchev, William V. Tamborlane, William T. Cefalu, and Claudio Cobelli. The artificial pancreas in 2016: A digital treatment ecosystem for diabetes. *Diabetes Care,* 39(7):1123-1126, 2016.

[2] Hood Thabit and Roman Hovorka. Coming of age: the artificial pancreas for type 1 diabetes. *Diabetologia,* 59(9):1795-1805, 2016.

[3] G. P. Forlenza, B. Buckingham, and et al. David M. Maahs. Progress in diabetes technology: Developments in insulin pumps, continuous glucose monitors, and progress towards the artificial pancreas. *The Journal of Pediatrics,* 169:13-20, feb 2016.

[4] Thomas Peyser, Eyal Dassau, Marc Breton, and Jay S. Skyler. The artificial pancreas: current status and future prospects in the management of diabetes. *Annals of the New York Academy of Sciences,* 1311(1):102-123, 2014.

[5] J. Pinsker, J. B. Lee, E. Dassau, and et al. Randomized crossover comparison of personalized mpc and pid control algorithms for the artificial pancreas. *Diabetes Care,* 39(7):1135-1142, jul 2016.

[6] S. Del Favero, D. Bruttomesso, F Di Palma, and et al. First use of model predictive control in outpatient wearable artificial pancreas. *Diabetes Care,* 37(5): 1212-1215, may 2014.

[7] F. D. Doyle, L. M. Huyett, and et al. J. B. Lee. Closed-loop artificial pancreas systems: Engineering the algorithms. *Diabetes Care,* 37(5):1191-1197, may 2014.

[8] C. C. Palerm, H. Zisser, L. Jovanovic, and F. J. Doyle III. A run-to-run control strategy to adjust basal insulin infusion rates in type 1 diabetes. *Journal of Process Control,* 18(3):258-265, 2008.

[9] C. Owens, H. Zisser, L. Jovanovic, B. Srinivasan, D. Bonvin, and F. J. Doyle III. Run-to-run control of blood glucose concentrations for people with type 1 diabetes mellitus. *IEEE Transactions in Biomedical Engineering,* 53(6):996-1005, 2006.

[10] C. Cobelli et al. C. Toffanin, M. Missori. Automatic adaptation of basal therapy for type 1 diabetic patients: A run-to-run approach. *Biomedical Signal Processing,* 31:539-549, jan 2017.

[11] Claudio Cobelli, Eric Renard, and Boris Kovatchev. Artificial pancreas: Past, present, future. *Diabetes,* 60(11):2672-2682, 2011.

[12] M. Laimer, A Melmer, J K Mader, and et al. Variability of basal rate profiles in insulin pump therapy and association with complications in type 1 diabetes mellitus. *PLoS ONE,* 11(3), 2016.

[13] C. Dalla Man, F. Micheletto, D. Lv, M. Breton, B. P. Kovatchev, and C. Cobelli. The uva/padova type 1 diabetes simulator: new features. *J. Diabetes Sci. Technol.,* 8(1):26-34, 2014.

[14] Ravi Gondhalekar, Eyal Dassau, and Francis J. Doyle III. Periodic zone-mpc with asymmetric costs for outpatient-ready safety of an artificial pancreas to treat type 1 diabetes. *Automatica,* 71:237-246, sep 2016.

[15] B P Kovatchev and W. Clarke. Statistical tools to analyze continuous glucose monitor data. *Diabetes Technology & Therapeutics,* 11(S1):545-S54, may 2009.

[16] Boris P. Kovatchev Boris, Erik Otto, Daniel Cox, Linda Gonder-Frederick, and William Clarke. Evaluation of a new measure of blood glucose variability in diabetes. *Diabetes Care,* 29(11):2433-2438, nov 2006.

The following patents, applications and publications as listed below and throughout this document are hereby incorporated by reference in their entirety herein. It should be appreciated that various aspects of embodiments of the present method, system, devices, article of manufacture, computer readable medium, and compositions may be implemented with the following methods, systems, devices, article of manufacture, computer readable medium, and compositions disclosed in the following U.S. Patent Applications, U.S. Patents, and PCT International Patent Applications and are hereby incorporated by reference herein and co-owned with the assignee (and which are not admitted to be prior art with respect to the present disclosure by inclusion in this section):

1. International Patent Application No. PCT/US2017/015616 entitled "METHOD, SYSTEM, AND COMPUTER READABLE MEDIUM FOR VIREALIZATION OF A CONTINUOUS GLUCOSE MONITORING TRACE", filed Jan. 30, 2017.
2. International Patent Application No. PCT/US2016/058234 entitled "System, Method and Computer Readable Medium for Dynamical Tracking of the Risk for Hypoglycemia in Type 1 and Type 2 Diabetes", filed Oct. 21, 2016.
3. International Patent Application No. PCT/US2016/054200 entitled "GAIT PATHOLOGY DETECTION AND MONITORING SYSTEM, AND METHOD", filed Sep. 28, 2016.
4. International Patent Application No. PCT/US2016/050109 entitled "SYSTEM, METHOD, AND COMPUTER READABLE MEDIUM FOR DYNAMIC INSULIN SENSITIVITY IN DIABETIC PUMP USERS", filed Sep. 2, 2016; U.S. patent application Ser. No. 15/255,828 entitled "SYSTEM, METHOD, AND COMPUTER READABLE MEDIUM FOR DYNAMIC INSULIN SENSITIVITY IN DIABETIC PUMP USERS", filed Sep. 2, 2016.
5. U.S. patent application Ser. No. 15/252,365 entitled "Method, System and Computer Readable Medium for Predictive Hypoglycemia Detection for Mild to Moderate Exercise", filed Aug. 31, 2016.
6. U.S. patent application Ser. No. 15/109,682 entitled "Central Data Exchange Node For System Monitoring and Control of Blood Glucose Levels in Diabetic Patients", filed Jul. 5, 2016; Publication No. US-2016-0331310-AI, Nov. 17, 2016; International Patent Application No. PCT/US2015/010167 entitled "Central Data Exchange Node For System Monitoring and Control of Blood Glucose Levels in Diabetic Patients", filed Jan. 5, 2015; Publication No. WO2015103543, Jul. 9, 2015.
7. International Patent Application No. PCT/US2016/036729 entitled "CGM Based Fault Detection and Mitigation of Insulin Delivery/Monitoring Systems Via Metabolic State Tracking", filed Jun. 9, 2016; Publication No. WO2016201120, Dec. 15, 2016.
8. International Patent Application No. PCT/US2016/036481 entitled "Hemoglobin A1c and Self-Monitored Average Glucose: Validation of the Dynamical Tracking A1c Algorithm in Type 1 Diabetes", filed Jun. 8, 2016; Publication No. WO2016200970, Dec. 15, 2016.
9. International Patent Application No. PCT/US2016/018027 entitled "Method, System and Computer Readable Medium for Assessing Actionable Glycemic Risk", filed Feb. 16, 2016; Publication No. WO2016133879, Aug. 25, 2016.
10. U.S. patent application Ser. No. 14/902,731 entitled "SIMULATION OF ENDOGENOUS AND EXOGENOUS LUCOSE/INSULIN/GLUCAGON INTERPLAY IN TYPE 1 DIABETIC PATIENTS", filed Jan. 4, 2016; Publication No. US-2016-0171183-A1, Jun. 16, 2016; International Patent Application No. PCT/US2014/045393 entitled "SIMULATION OF ENDOGENOUS AND EXOGENOUS LUCOSE/INSULIN/GLUCAGON INTERPLAY IN TYPE 1 DIABETIC PATIENTS", filed Jul. 3, 2014; Publication No. WO2015003124, Jan. 8, 2015.
11. U.S. patent application Ser. No. 14/769,638 entitled "METHOD AND SYSTEM FOR MODEL-BASED TRACKING OF CHANGES IN AVERAGE GLYCEMIA IN DIABETES", filed Aug. 21, 2015; Publication No. US-2016-0004813-A1, Jan. 7, 2016; International Patent Application No. PCT/US2014/017754 entitled "METHOD AND SYSTEM FOR MODEL-BASED TRACKING OF CHANGES IN AVERAGE GLYCEMIA IN DIABETES", filed Feb. 21, 2014; Publication No. WO 2014/130841, Aug. 28, 2014.
12. International Patent Application No. PCT/US2015/045340 entitled "IMPROVED ACCURACY CONTINUOUS GLUCOSE MONITORING METHOD, SYSTEM, AND DEVICE", filed Aug. 14, 2015; Publication No. WO2016025874, Feb. 18, 2016.
13. U.S. patent application Ser. No. 14/799,329 entitled "Improving the Accuracy of Continuous Glucose Sensors", filed Jul. 14, 2015; Publication No. US-2016-0007890-A1, Jan. 14, 2016; U.S. patent application Ser. No. 12/065,257 entitled "Accuracy of Continuous Glucose Sensors", filed Feb. 28, 2008; Publication No. 2008/0314395, Dec. 25, 2008; International Patent Application No. PCT/US2006/033724 entitled "Method for Improvising Accuracy of Continuous Glucose Sensors and a Continuous Glucose Sensor Using the Same", filed Aug. 29, 2006; Publication No. WO07027691, Mar. 8, 2007.
14. U.S. patent application Ser. No. 14/419,375 entitled "COMPUTER SIMULATION FOR TESTING AND MONITORING OF TREATMENT STRATEGIES FOR STRESS HYPERGLYCEMIA", filed Feb. 3, 2015; Publication No. 2015-0193589, Jul. 9, 2015; International Patent Application No. PCT/US2013/053664 entitled "COMPUTER SIMULATION FOR TESTING AND MONITORING OF TREATMENT STRATEGIES FOR STRESS HYPERGLYCEMIA", filed Aug. 5, 2013; Publication No. WO 2014/022864, Feb. 6, 2014.
15. U.S. patent application Ser. No. 14/266,612 entitled "Method, System and Computer Program Product for Real-Time Detection of Sensitivity Decline in Analyte Sensors", filed Apr. 30, 2014; Publication No. 2014/0244216, Aug. 28, 2014; U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014; U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012; International Patent Application No. PCT/US2007/082744 entitled "Method, System and Computer Program Product for Real-Time Detection of Sensitivity Decline in Analyte Sensors", filed Oct. 26, 2007; Publication No. WO/2008/052199, May 2, 2008.
16. U.S. patent application Ser. No. 14/241,383 entitled "Method, System and Computer Readable Medium for Adaptive Advisory Control of Diabetes", filed Feb. 26, 2014; Publication No. 2015-0190098, Jul. 9, 2015; International Patent Application No. PCT/US2012/052422 entitled "Method, System and Computer Readable Medium for Adaptive Advisory Control of Diabetes", filed Aug. 26, 2012; Publication No. WO 2013/032965, Mar. 7, 2013.

17. U.S. patent application Ser. No. 14/128,922 entitled "Unified Platform For Monitoring and Control of Blood Glucose Levels in Diabetic Patients", filed Dec. 23, 2013; Publication No. 2015/0018633, Jan. 15, 2015; International Patent Application No. PCT/US2012/043910 entitled "Unified Platform For Monitoring and Control of Blood Glucose Levels in Diabetic Patients", filed Jun. 23, 2012; Publication No. WO 2012/178134, Dec. 27, 2012.

18. U.S. patent application Ser. No. 14/128,811 entitled "Methods and Apparatus for Modular Power Management and Protection of Critical Services in Ambulatory Medical Devices", filed Dec. 23, 2013; U.S. Pat. No. 9,430,022, issued Aug. 30, 2016; International Patent Application No. PCT/US2012/043883 entitled "Methods and Apparatus for Modular Power Management and Protection of Critical Services in Ambulatory Medical Devices", filed Jun. 22, 2012; Publication No. WO 2012/178113, Dec. 27, 2012.

19. U.S. patent application Ser. No. 14/015,831 entitled "CGM-Based Prevention of Hypoglycemia Via Hypoglycemia Risk Assessment and Smooth Reduction Insulin Delivery", filed Aug. 30, 2013; Publication No. 20140046159, Feb. 13, 2014; U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013; International Patent Application No. PCT/US2010/025405 entitled "CGM-Based Prevention of Hypoglycemia via Hypoglycemia Risk Assessment and Smooth Reduction Insulin Delivery", filed Feb. 25, 2010; Publication No. WO 2010/099313 A1, Sep. 2, 2010.

20. International Patent Application No. PCT/US2013/042745 entitled "INSULIN-PRAMLINTIDE COMPOSITIONS AND METHODS FOR MAKING AND USING THEM", filed May 24, 2013; Publication No. WO 2013/177565, Nov. 28, 2013; U.S. Patent Application No. entitled "INSULIN-PRAMLINTIDE COMPOSITIONS AND METHODS FOR MAKING AND USING THEM".

21. U.S. patent application Ser. No. 13/637,359 entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Sep. 25, 2012; U.S. Pat. No. 9,398,869, issued Jul. 26, 2016; International Patent Application No. PCT/US2011/029793 entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Mar. 24, 2011; Publication No. WO 2011/119832, Sep. 29, 2011.

22. U.S. patent application Ser. No. 13/634,040 entitled "Method and System for the Safety, Analysis, and Supervision of Insulin Pump Action and Other Modes of Insulin Delivery in Diabetes", filed Sep. 11, 2012; Publication No. 2013/0116649, May 9, 2013; International Patent Application No. PCT/US2011/028163 entitled "Method and System for the Safety, Analysis, and Supervision of Insulin Pump Action and Other Modes of Insulin Delivery in Diabetes", filed Mar. 11, 2011; Publication No. WO 2011/112974, Sep. 15, 2011.

23. U.S. patent application Ser. No. 13/394,091 entitled "Tracking the Probability for Imminent Hypoglycemia in Diabetes from Self-Monitoring Blood Glucose (SMBG) Data", filed Mar. 2, 2012; Publication No. 2012/0191361, Jul. 26, 2012; International Patent Application No. PCT/US2010/047711 entitled "Tracking the Probability for Imminent Hypoglycemia in Diabetes from Self-Monitoring Blood Glucose (SMBG) Data", filed Sep. 2, 2010; Publication No. WO 2011/028925, Mar. 10, 2011.

24. U.S. patent application Ser. No. 13/393,647 entitled "System, Method and Computer Program Product for Adjustment of Insulin Delivery (AID) in Diabetes Using Nominal Open-Loop Profiles", filed Mar. 1, 2012; Publication No. 2012/0245556, Sep. 27, 2012; International Patent Application No. PCT/US2010/047386 entitled "System, Method and Computer Program Product for Adjustment of Insulin Delivery (AID) in Diabetes Using Nominal Open-Loop Profiles", filed Aug. 31, 2010; Publication No. WO 2011/028731, Mar. 10, 2011.

25. U.S. patent application Ser. No. 13/380,839 entitled "System, Method, and Computer Simulation Environment for In Silico Trials in Pre-Diabetes and Type 2 Diabetes", filed Dec. 25, 2011; Publication No. 2012/0130698, May 24, 2012; International Patent Application No. PCT/US2010/040097 entitled "System, Method, and Computer Simulation Environment for In Silico Trials in Prediabetes and Type 2 Diabetes", filed Jun. 25, 2010; Publication No. WO 2010/151834, Dec. 29, 2010.

26. U.S. patent application Ser. No. 13/322,943 entitled "System Coordinator and Modular Architecture for Open-Loop and Closed-Loop Control of Diabetes", filed Nov. 29, 2011; Publication No. 2012/0078067, Mar. 29, 2012; International Patent Application No. PCT/US2010/036629 entitled "System Coordinator and Modular Architecture for Open-Loop and Closed-Loop Control of Diabetes", filed May 28, 2010; Publication No. WO 2010/138848, Dec. 2, 2010.

27. U.S. patent application Ser. No. 13/131,467 entitled "Method, System, and Computer Program Product for Tracking of Blood Glucose Variability in Diabetes", filed May 26, 2011; U.S. Pat. No. 9,317,657, issued Apr. 19, 2016; International Patent Application No. PCT/US2009/065725 entitled "Method, System, and Computer Program Product for Tracking of Blood Glucose Variability in Diabetes", filed Nov. 24, 2009; Publication No. WO 2010/062898, Jun. 3, 2010.

28. U.S. patent application Ser. No. 12/975,580 entitled "Method, System, and Computer Program Product for the Evaluation of Glycemic Control in Diabetes from Self-Monitoring Data", filed Dec. 22, 2010; Publication No. 2012/0004512, Jan. 5, 2012; U.S. patent application Ser. No. 11/305,946 entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011; U.S. patent application Ser. No. 10/240,228 entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006; International Patent Application No. PCT/US2001/009884 entitled "Method, System, and Computer Program Product for the Evaluation of Glycemic Control in Diabetes", filed Mar. 29, 2001; Publication No. WO 01/72208, Oct. 4, 2001.

29. U.S. patent application Ser. No. 12/665,420 entitled "LQG Artificial Pancreas Control System and Related Method", filed Dec. 18, 2009; Publication No. 2010/0249561, Sep. 30, 2010; International Patent Application No. PCT/US2008/067723 entitled "LQG Artificial Pancreas Control System and Related Method", filed Jun. 20, 2008; Publication No. WO 2008/157780, Dec. 24, 2008.
30. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; Publication No. 2010/0198520, Aug. 5, 2010; International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; Publication No. WO 2009/009528, Jan. 15, 2009.
31. U.S. patent application Ser. No. 12/664,444 entitled "Method, System and Computer Simulation Environment for Testing of Monitoring and Control Strategies in Diabetes", filed Dec. 14, 2009; Publication No. 2010/0179768, Jul. 15, 2010; International Patent Application No. PCT/US2008/067725 entitled "Method, System and Computer Simulation Environment for Testing of Monitoring and Control Strategies in Diabetes", filed Jun. 20, 2008; Publication No. WO 2008/157781, Dec. 24, 2008.
32. U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013; International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; Publication No. WO2008/067284, Jun. 5, 2008.
33. U.S. patent application Ser. No. 12/159,891 entitled "Method, System and Computer Program Product for Evaluation of Blood Glucose Variability in Diabetes from Self-Monitoring Data", filed Jul. 2, 2008; Publication No. 2009/0171589, Jul. 2, 2009; International Patent Application No. PCT/US2007/000370 entitled "Method, System and Computer Program Product for Evaluation of Blood Glucose Variability in Diabetes from Self-Monitoring Data", filed Jan. 5, 2007; Publication No. WO07081853, Jul. 19, 2007.
34. U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; Publication No. 2008/0154513, Jun. 26, 2008.
35. U.S. patent application Ser. No. 11/578,831 entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010; International Patent Application No. US2005/013792 entitled "Method, System and Computer Program Product for Evaluating the Accuracy of Blood Glucose Monitoring Sensors/Devices", filed Apr. 21, 2005; Publication No. WO05106017, Nov. 10, 2005.
36. U.S. patent application Ser. No. 10/524,094 entitled "Method, System, And Computer Program Product For The Processing Of Self-Monitoring Blood Glucose (SMBG) Data To Enhance Diabetic Self-Management", filed Feb. 9, 2005; Publication No. 2005214892, Sep. 29, 2005; International Patent Application No. PCT/US2003/025053 entitled "Managing and Processing Self-Monitoring Blood Glucose", filed Aug. 8, 2003; Publication No. WO 2004/015539, Feb. 19, 2004.
37. U.S. patent application Ser. No. 10/069,674 entitled "Method and Apparatus for Predicting the Risk of Hypoglycemia", filed Feb. 22, 2002; U.S. Pat. No. 6,923,763, issued Aug. 2, 2005; International Patent Application No. US00/22886 entitled "METHOD AND APPARATUS FOR PREDICTING THE RISK OF HYPOGLYCEMIA", filed Aug. 21, 2000; Publication No. WO01/13786, Mar. 1, 2001.

SUMMARY

An insulin device configured to control an insulin dosage by adapting a basal rate profile is disclosed, the insulin device includes: a sensor configured to produce a blood glucose level measurement data, and detect changes of the blood glucose level measurement data over time; a processor and associated computer memory device configured to receive the blood glucose level measurement data and a basal rate profile, wherein the basal rate profile includes a basal rate set point that corresponds to an insulin delivery reference for a nominal blood glucose, and wherein the basal rate profile is stored in the computer memory device; and an insulin dispensing valve controlled by the processor to administer insulin in accordance with the received basal rate profile, wherein the processor is configured to update the basal rate set point over a time period based on both an assessment of at least one of a risk of hyperglycemia and a risk of hypoglycemia from historical blood glucose data, and patterns of actions taken by the insulin device to mitigate glycemic risk during the time period, and wherein the insulin dispensing valve is controlled by the processor to administer insulin in accordance with the updated basal rate set point.

A computer-implemented method to control an insulin dosage by adapting a basal rate profile is disclosed, the method includes: producing a blood glucose level measurement data; detecting changes of the blood glucose level measurement data over time; receiving the blood glucose level measurement data and a basal rate profile, wherein the basal rate profile includes a basal rate set point that corresponds to an insulin delivery reference for a nominal blood glucose, and wherein the basal rate profile is stored in the computer memory device; administering insulin in accordance with the received basal rate profile; updating the basal rate set point over a time period based on both an assessment of at least one of a risk of hyperglycemia and a risk of hypoglycemia from historical blood glucose data, and patterns of actions taken by the insulin device to mitigate glycemic risk during the time period; and controlling an insulin dispensing device to provide insulin dosing based on the updated basal rate set point.

A non-transitory computer readable recording medium encoded with a computer program is disclosed comprising program instructions for causing an insulin device to control an insulin dosage by adapting a basal rate profile, the computer program causing the insulin device to: produce a blood glucose level measurement data; detect changes of the blood glucose level measurement data over time; receive the blood glucose level measurement data and a basal rate profile, wherein the basal rate profile includes a basal rate set point that corresponds to an insulin delivery reference for a nominal blood glucose, and wherein the basal rate profile is stored in the computer memory device; administer insulin in accordance with the received basal rate profile; update the basal rate set point over a time period based on both an assessment of at least one of a risk of hyperglycemia and a risk of hypoglycemia from historical blood glucose data, and patterns of actions taken by the insulin device to mitigate glycemic risk during the time period; and control an insulin dispensing device to provide insulin dosing based on the updated basal rate profile.

BRIEF DESCRIPTION OF THE DRAWINGS

Other objects and advantages of the present disclosure will become apparent to those skilled in the art upon reading the following detailed description of exemplary embodiments, in conjunction with the accompanying drawings, in which like reference numerals have been used to designate like elements, and in which.

DETAILED DESCRIPTION

Figure 1:
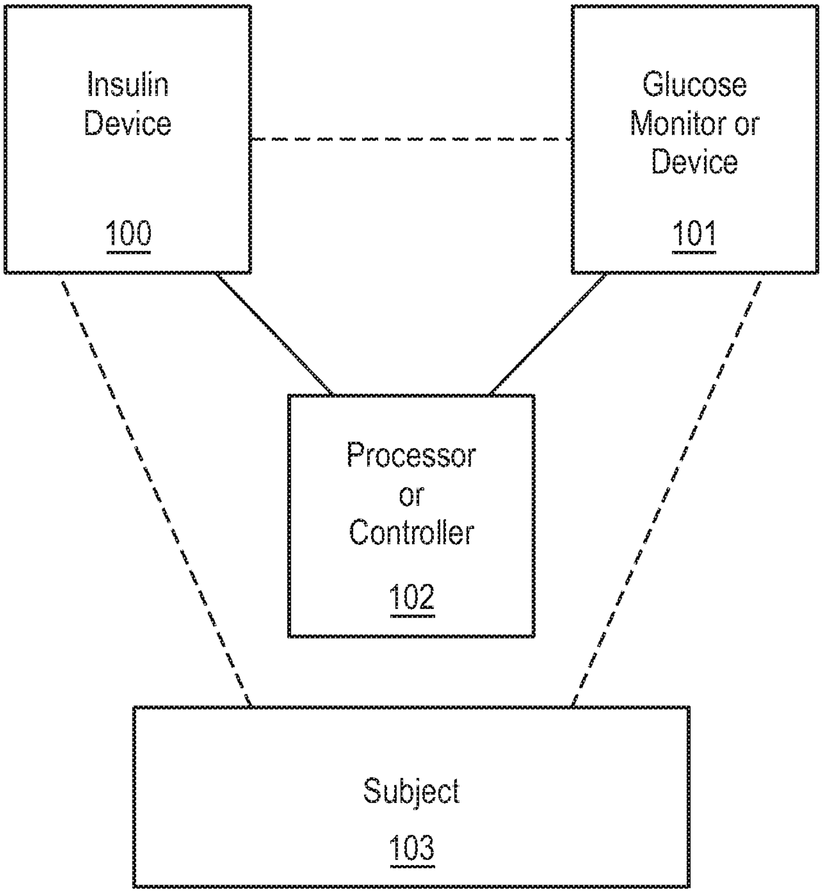
FIG. 1 is a high level functional block diagram of an exemplary embodiment of the present disclosure, or an aspect of an exemplary embodiment of the present disclosure.

The present disclosure is directed to providing an improved insulin device (method, and computer readable medium) configured to control insulin dispensing based on adaptation of a basal rate profile. The device uses an adaptation algorithm for the artificial pancreas which uses CGM readings and the controller's insulin infusion data to adjust the basal profile parameter over the course of multi-day runs. The algorithm is tested in silico using the 100 adult subjects in UVa/Padova type 1 diabetes simualtor running a zone model predictive control (ZMPC) controller over 42 total days with varying meal sizes, numbers, and timings, under both heuristically set and algorithmically adapted basal profiles. Results are compared.

In silico subjects showed statistically significant improvements in several varying clinical metrics (mean BG, LBGI, HBGI, time BG>180 mg/dl, etc.) without any statistically significant degradation in others for profiles adapted from ±20% of a baseline heuristic profile. With initial profile 140% of baseline, performance in several metrics for hypoglycemic risk improved (ADRR, LBGI, time BG<70 mg/dl), though with elevated mean BG readings compared to the control.

The described basal profile adaptation algorithm uses both historical CGM data and controller action to determine adjustments to the basal insulin profile by a methodology agnostic the specific mechanism of the AP controller. In silico testing of the proposed basal rate profile adaptation algorithm shows statistically significant performance improvements in several different metrics for the adapted versus initial profiles withing 20% of the baseline heuristic profile. The device can administer insulin to a patient in a more effective manner by using the basal profile adaptation algorithm disclosed herein to provide the optimal amount of insulin at an optimal time.

A focus herein is on the daily "basal insulin delivery rate" parameter in AP systems and our purpose is to present an algorithmic methodology for iteratively adapting and thus individualizing this parameter in a "run-to-run" style framework for subjects using an AP system. Generally, treatment regimes for diabetes consist of both bolus insulin, which accounts for the carbohydrates ingested with meals or is used to correct acute hyperglycemic excursions, and basal insulin, which is given to maintain proper blood glucose levels throughout the day. Currently, clinical treatment of diabetes either involves delivering basal insulin by means of multiple daily injections of slow acting insulin (MDI) given manually by the subject or their caregiver or via subcutaneous insulin infusion (CSII) or "pump" therapy—where an insulin pump pseudo-continuously (usually in five minute intervals) delivers short-acting insulin into the subject's subcutaneous tissue throughout the day to account for their basal insulin needs. Since insulin sensitivity, internal glucose production, or other factors contributing to blood glucose levels may not be constant over the course of the day, pump based therapy delivers basal insulin according to a possibly time-varying rate determined by the basal profile. Due to the large degree of inter-patient variability in insulin needs, this basal profile must be individually set by the patient and their physician, usually via heuristic clinical rules and intuitively determined, evidence based adjustments. The resulting treatment paradigm involves continuous delivery of basal insulin according to the pre-set profile, with users delivering meal-related or correction boluses of insulin or temporarily adjusting the basal rate itself to control the blood glucose levels.

In the case of AP systems, short acting insulin is delivered throughout the day automatically, and is usually conceived as a differential dosage being delivered at a given time at, below, or above the anchoring basal rate given by the basal profile parameter. This differential dosage may be determined algorithmically according to feedback rules based on sensor data, estimated projections of the future path of the system state, or feed-forward rules using user input of "meal announcements" or correction boluses. In this framework the "basal-rate" serves as an orienting parameter which sets the default amount of insulin to be delivered by the AP, and even though the actual decision of how much insulin is given will, under operating circumstances, be determined by the AP algorithm and is not necessarily the amount indicated by the basal rate profile itself, the basal rate may restrict and inform the course of action the AP is allowed to take. Thus even though the AP system delivers insulin "automatically", the question arises as to whether there is an effective, algorithmic way to adjust the basal profile to promote better treatment outcomes under an AP system.

Use of "run-to-run" methods to adjust basal profiles in the context of "open-loop" pump therapy have been explored before (see documents "[8]" Palerm et al, "[9]" Owens et al, and "[10]" Cobelli et al), and we propose an algorithm which applies a "run-to-run" inspired approach to adjust basal profiles for patients being treated under an AP system. This method uses both continuous glucose measurements as well as the historical record of insulin delivered by the AP controller to iteratively determine adjustments to the basal profile. The potential advantages of this method, above any direct gains in treatment outcome resulting from a individualized profile adjusted with the algorithm, lie in its modularity and agnosticism to the mechanism of the underlying AP controller. The basal adaptation algorithm as conceived can work as an add-on module to any controller: MPC, PD, PID, etc. which uses a basal insulin delivery rate as an underlying parameter, and would be able to integrate with the AP system regardless of the exact operations of the AP's control algorithm. A more detailed exposition of this "basal adaptation" algorithm is presented in the following section.

In open loop sub-cutaneous insulin infusion pump therapy—the closest analogue to the proposed artificial pancreas framework currently widely used in practice—the basal insulin rate varies to accommodate differences in insulin needs due to diurnal changes in insulin sensitivity, endogenous glycogenesis in the liver and other organs, as well as any other sources of daily periodic variation in basal insulin needs. These rates are usually set initially by heuristic methods and adjusted by the patient and their physician in a trial-and-error process. As closed-loop systems are implemented to automate insulin delivery, the natural extension of this process would be to automate the adjustment of the underlying system parameters as well: the basal profile, carbohydrate ratio, or correction factor. The need for adjustment in the basal profile in particular is seen from in silico explorations that indicate the potential for oscillatory and other unstable dynamics to occur under closed-loop control if the basal rate is maladjusted. These phenomena may lead to instability in the closed-loop system, causing incidents of hypoglycemia along with extended periods of hyperglycemia.

Given the current nature of AP development, a modular approach to system designs is, for example, preferred (see document "[11]" Cobelli et al), thus algorithmic procedures for adjusting system parameters which can operate without needing specific knowledge of the AP's particular control methodology are, for example, preferable unless and until the AP control methodology is standardized. We propose an automated, iterative algorithmic process by which to set the basal profile for any closed-loop AP system for which the profile is an adjustable parameter and that is agnostic to the specific underlying controller mechanism. So, regardless of the nature of that algorithm (PID, PD, MPC, etc.) iterative recommendations for basal profile adjustments can be generated which does not require access to any of the AP controller's specific operations or potentially proprietary code.

The present disclosure is directed to providing an improved insulin device, method, and computer readable medium configured to control an insulin dosage by adapting a basal rate profile by using an algorithm for basal profile adjustment. According to the algorithm, the time varying basal rate is denoted with the functional notation B(t). In most cases B(t) is a step-wise constant periodic function. From the nature of the insulin delivery process we can assume t to take discrete values corresponding to five minute intervals throughout the day with daily periodic repetition. Thus the day can be divided into 288 distinct time periods. For example, to have a basal rate of insulin delivery which is set to give 0.5 units of insulin per hour from midnight until six A.M., 0.9 units per hour from six A.M. until noon, and 0.8 units per hour from noon until the following midnight, the profile can be written as:

$$B(t) = \begin{cases} 0.0417 & 0 \le t < 72 \\ 0.075 & 72 \le t < 144 \\ 0.0667 & 144 \le t \le 287, \end{cases}$$

with the periodic restriction that B(t+288)=B(t) extending the profile function over any amount of time. The framework for adjustment of the patients basal profile is based on the "run-to-run" methodology from batch process engineering—data from a previous week of treatment is used to determine the proper adjustment of the profile to be implemented in the next week, and this process is iteratively continued on for further weeks. The length of this run can generally be taken to be a regular seven day week. The two driving factors in our adjustment procedure are times of hypoglycemic or hyperglycemic "risk" as assessed by a risk function and consistent deviations of the non-meal related insulin delivered in the course of the run at below or above the basal rate.

Figure 4:
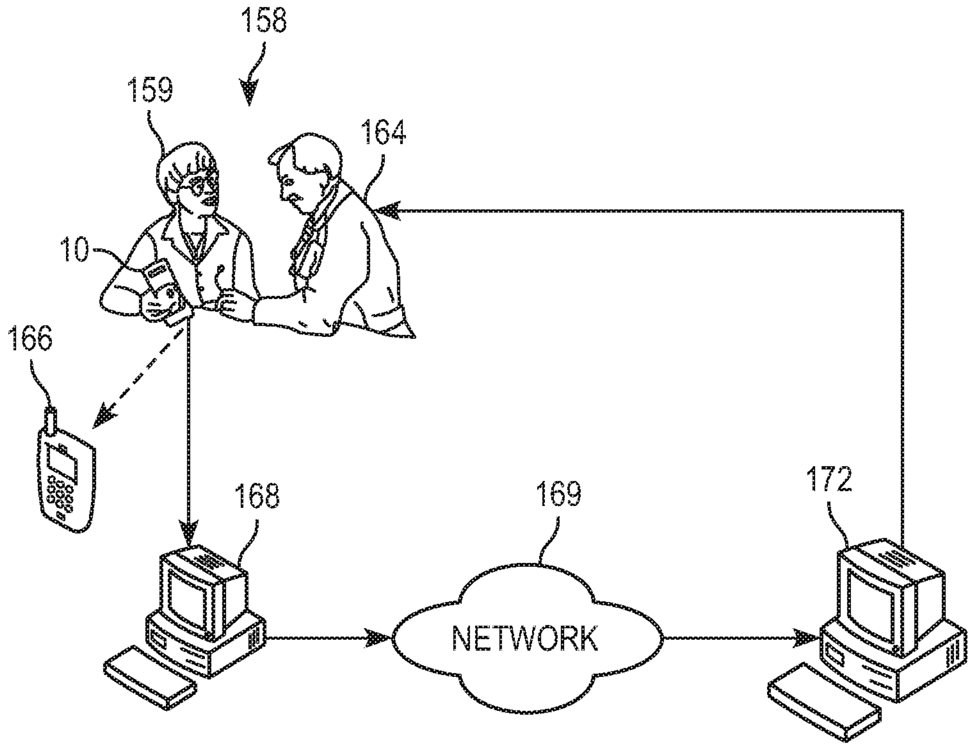
FIG. 4 illustrates a system in which one or more embodiments of the disclosure can be implemented using a network, or portions of a network or computers.
Figure 5:
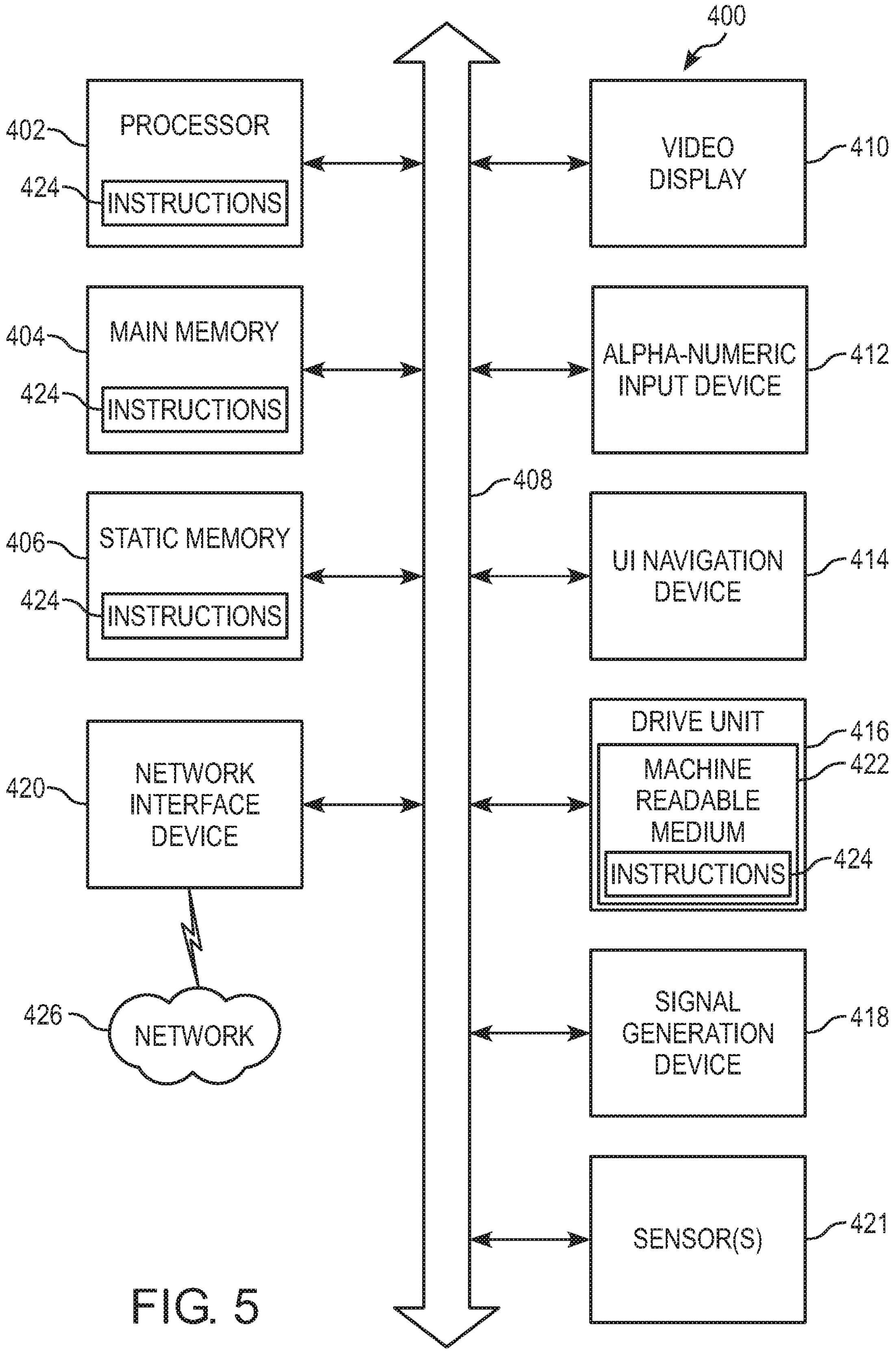
FIG. 5 is a block diagram illustrating an example of a machine upon which one or more aspects of embodiments of the present disclosure can be implemented.

A sensor configured to produce a blood glucose level measurement data, and detect changes of the blood glucose level measurement data over time. In an embodiment the glucose monitor 101 or glucose meter (and/or insulin pump) may be implemented by the subject (or patient) locally at home or other desired location. However, in an alternative embodiment it may be implemented in a clinic setting or assistance setting. For instance, referring to FIG. 4, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system of the disclosure and any component thereof may be used in the manner depicted by FIG. 4. The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples of the disclosure can also be implemented in a standalone computing device associated with the target glucose monitoring device. An exemplary computing device (or portions thereof) in which examples of the disclosure can be implemented is schematically illustrated in FIG. 2A.

A processor 102 and associated computer memory device is configured to receive the blood glucose level measurement data and a basal rate profile, such that the basal rate profile includes a basal rate set point that corresponds to an insulin delivery reference for a nominal blood glucose level, and the basal rate profile is stored in the computer memory device. The processor 102 is configured to receive the historical blood glucose data from an artificial pancreas. The processor is configured to receive the historical blood glucose data by a manual input. The basal rate set point is a point at which a basal rate tends to stabilize. The nominal blood glucose level is the amount of glucose normally present in the blood. As shown in FIG. 1, a processor or controller 102 communicates with the glucose monitor or device 101, and optionally the insulin device 100. The glucose monitor or device 101 communicates with the subject 103 to monitor glucose levels of the subject 103. The processor or controller 102 is configured to perform the required calculations. Optionally, the insulin device 100 communicates with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Figure 2A:
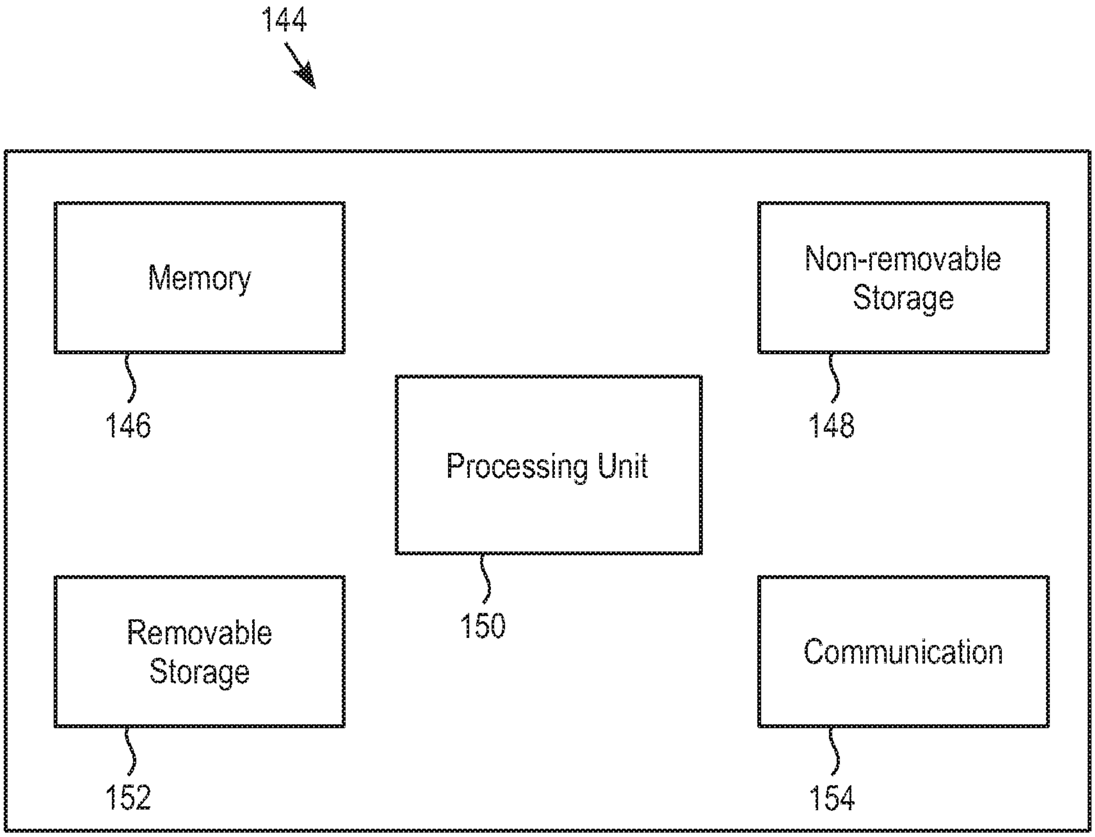
FIG. 2A illustrates a computing device in upon which an embodiment of the disclosure can be implemented.

Referring to FIG. 2A, in an exemplary configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media can embody computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

In an exemplary embodiment, the insulin dosage can be administered using an insulin dispensing valve that is controlled by the processor 102 to administer insulin in accordance with the received basal rate profile. In an exemplary embodiment, the insulin dispensing valve has a retractable needle cannula and can be attached to the insulin device.

In an exemplary embodiment, the processor 102 is configured to update the basal rate set point over a time period based on both an assessment of at least one of a risk of hyperglycemia and a risk of hypoglycemia from historical blood glucose data, and patterns of actions taken by the insulin device to mitigate glycemic risk during the time period. The processor uses the algorithm disclosed herein to update the basal rate set point. As a first step, the processor 102 initializes parameters. These parameters include the thresholds for assessing periods of high and low blood glucose risks by our risk function, denoted BGhi and BGlo respectively, the minimum length of time which is allowed to constitute an actionable "risk zone" (to be defined shortly) for either hyper- or hypoglycemia, as well as a "zone attribution perimeter" (ZAP) which determines how the overall changes in basal rate should be weighted towards the above mentioned "risk zones" as opposed to overall "across-the-board" adjustments. In addition, both the continuous glucose monitor (CGM) traces and record of non-meal related insulin delivered (i.e. insulin history—excluding meal-related boluses) over the course of the run preceding the adaption are gathered and prepared (if necessary: cleaned, filtered, interpolated, etc.) for use by the algorithm.

The CGM blood glucose trace is used to ascertain periods of actionable hyper- and hypoglycemic risks. The risk function used to categorize periods of time is determined by the parameters BGhi and BGlo, indicating hyper and hypoglycemic risk thresholds, respectively.

Assume that at a given time t the CGM blood glucose reading will be denoted BG(t), the risk at time t, BGrisk(t) is then given by:

$$BG_{risk}(t) = \frac{1}{\log\left(\sqrt{\frac{BG_{lo}}{BG_{hi}}}\right)^2} \cdot \log\left(\frac{BG(t)}{\sqrt{BG_{hi} \cdot BG_{lo}}}\right)^2.$$

The output of this function is partitioned depending on whether or not it identifies hyper or hypoglycemic risk. Thus:

$$BG_{riskHi}(t) = \begin{cases} BG_{risk}(t) & BG_{risk}(t) \geq \sqrt{BG_{hi} \cdot BG_{lo}} \\ 0 & \text{otherwise,} \end{cases}$$

$$\text{While: } BG_{riskLow}(t) = \begin{cases} BG_{risk}(t) & BG_{risk}(t) < \sqrt{BG_{hi} \cdot BG_{lo}} \\ 0 & \text{otherwise,} \end{cases}$$

To identify opportunities to mitigate hyper or hypoglycemic risk the processor is configured to determine the risk of hyperglycemia by measuring a first moving average of a high blood glucose risk function for a plurality of first time periods and computing an average of the measured first moving average, and determine the risk of hypoglycemia by measuring a second moving average of a low blood glucose risk function for the plurality of first time periods and computing an average of the measured second moving average. For example, two hour moving averages of these high and low blood glucose risk functions can be taken for each day in the run and then compute the average of these values over the week. The resulting functions of the time t of any given day are considered indicative of low and high blood sugar risk mitigation opportunities $L_{op}(t)$ and $H_{op}(t)$, respectively. The total risk for a given time is thus a function $T_{op}=L_{op}+H_{op}$.

The magnitudes of chronic hyper and hypoglycemic risks can be considered which are potentially addressable by alterations of the basal profile to be indicated preliminarily by the functions (here with Add indicating that it is "addressable" risk):

$$Add^{*}_{Hypo}(t) = \max\left(0, L_{op} \cdot \frac{L_{op} - H_{op}}{T_{op}}\right), \text{ and}$$

$$Add^{*}_{Hyper}(t) = \max\left(0, H_{op} \cdot \frac{H_{op} - L_{op}}{T_{op}}\right)$$

The processor is configured to determine the risk of hyperglycemia and the risk of hypoglycemia during a same time period, and counterpoise the determined risks by updating the basal rate set point. For example, since it is possible that a subject experiences both hyper and hypoglycemia at the same time of the day over the course of a run (say risk of hyperglycemia at 10:00 on Tuesday, but risk of hypoglycemia at 10:00 on Friday), addressing even consistent low or high blood glucose incidents can be preempted by adjusting the basal rate when counterpoising risks are present during the same time period. Thus, a function is provided which indicates this "unaddressable risk". Unaddressable risk is given in functional form as:

$$UnAdd(t) = \frac{T_{op}(t) - Add^{*}_{Hypo}(t) - Add^{*}_{Hyper}(t)}{2}.$$

If this unaddressable risk is greater than a chosen threshold value at time t, we cap $Add^{*}_{Hypo}(t)$ and $Add^{*}_{Hyper}(t)$ below the preset threshold values which triggers the indication of a risk zone and modify the addressable risk functions. In the instantiation of the algorithm used for the simulation study below this threshold cap is set at 1. With this setting, the resulting form of the $Add_{Hypo}$ and $Add_{Hyper}$ functions are:

$$Add_{Hypo}(t) = \begin{cases} \max\left(0, L_{op} \cdot \frac{L_{op} - H_{op}}{T_{op}}\right) & UnAdd(t) < 1 \\ \min\left(1, L_{op} \cdot \frac{L_{op} - H_{op}}{T_{op}}\right) & \text{otherwise.} \end{cases}$$

and $$Add_{Hyper}(t) = \begin{cases} \max\left(0, H_{op} \cdot \frac{H_{op} - L_{op}}{T_{op}}\right) & UnAdd(t) < 1 \\ \min\left(1, H_{op} \cdot \frac{H_{op} - L_{op}}{T_{op}}\right) & \text{otherwise.} \end{cases}$$

The total deviations in insulin delivered both blow and above the basal rate during closed loop control over the course of the run are calculated. To denote this process let I(t) be the non-mean insulin delivered by the control algorithm at time t. Then let $I_{\%}(t)$ indicate the percentile of insulin delivered at time t over the course of the run. Threshold percentage values $\text{Percentile}_{low}$ and $\text{Percentile}_{hi}$ are chosen in order to chronic deviations from the basal profile then:

$$Delivered_{above}(t) = \begin{cases} I_{Percentile_{hi}}(t) - B(t) & I(t) > B(t) \\ 0 & \text{otherwise,} \end{cases}$$

$$\text{While } Delivered_{below}(t) = \begin{cases} B(t) - I_{Percentile_{Law}}(t) & I(t) < B(t) \\ 0 & \text{otherwise.} \end{cases}$$

The total insulin delivered above the basal rate is simply the integral of $\text{Delivered}_{above}(t)$ function over the course of the run (from say time $t_{start}$ to time $t_{end}$). That is:

$$\text{Total}_{above} = \int_{t_{start}}^{t_{end}} \text{Delivered}_{above}(t)dt.$$

Likewise the total insulin delivered below the basal rate during the run is given by:

$$\text{Total}_{below} = \int_{t_{start}}^{t_{end}} \text{Delivered}_{below}(t)dt.$$

All of the addressable hyper and hypoglycemic risk zones, $\text{Zone}_{HypoRisk}$, $\text{Zone}_{HyperRisk}$ are found. These zones are defined by the actionable hyper and hypoglycemic risk functions and the preset parameters indicating the threshold for actionable risks $T_{risks}$ and the minimum allowable size of hyper and hypoglycemic risk zone $R_{hypo}$ and $R_{hyper}$. Using this notation intervals T* falling into hyper and hypoglycemic risk zones are defined as the following:

$$\text{Zone}_{HyperRisk} = \{T^{*} | \text{Add}_{Hyper}(T^{*}) > T_{risks} \,\&\, |T^{*}| > R_{hyper}\},$$

$$\text{Zone}_{HypoRisk} = \{T^{*} | \text{Add}_{Hypo}(T^{*}) > T_{risks} \,\&\, |T^{*}| > R_{hypo}\}.$$

The algorithm can be biased towards mitigating hypoglycemic over hyperglycemic risks. For example, the processor is configured to mitigate the risk of hypoglycemia by updating the basal rate set point when both the risks of hyperglycemia and hypoglycemia are determined. Additionally, the processor is configured to, after the risk of hypoglycemia is mitigated, mitigate the risk of hyperglycemia by updating the basal rate set point.

Thus a first scan through the CGM trace is to find if $\text{Zone}_{HypoRisk}=\emptyset$. If $\text{Zone}_{HypoRisk}$ is non-empty and $\text{Total}_{below}>\text{Total}_{above}$ (i.e. the control algorithm is consistently delivering doses of insulin which are under that which would be delivered if the basal rate were strictly followed), then a check can be performed if a potential reduction in the basal rate is warranted.

If there are times in $\text{Zone}_{HypoRisk}$ where the upper percentile of insulin delivered is less than the current basal rate $I_{percentilehi}(t)<B(t)$ a reduction in the basal rate is determined to be warranted. Such actionable zones will be denoted by $\text{Zone}^*_{HypoRisk}$. The overall quantity of the reduction, a, is determined by total deviation below basal less the total deviation above, $\text{Total}_{below}-\text{Total}_{above}$ divided by the total of basal insulin which would be in the actionable $\text{Zone}^*_{HypoRisks}$ if the basal profile was followed exactly. In short:

$$\alpha = \frac{Total_{below} - Total_{above}}{\int_{Zone_{HypoRisks}} B(t)dt}.$$

The "raw" new basal profile recommendation will then be given by $$B^*_{new}(t) = B(t)\left(1 - \alpha \cdot \delta_{Zone^*_{HypoRtake}}(t)\right),$$

where $$\delta_S(t) = \begin{cases} 1 & t \in S \\ ZAP & \text{otherwise,} \end{cases}$$

where "ZAP" is the chosen zone attribution parameter. This parameter indicates how much the change in basal rate should be concentrated on the specific risk zones as opposed to an overall shift in the profile. In the case of a triggered reduction, the algorithm will tend to shift the overall profile as a whole, since a general deviation by the algorithm below the basal rate is taken to indicate that the basal rate profile is itself set too high (likewise, a general deviation above would indicate a basal rate profile generally too low) but, by using this zone attribution parameter, more weight may be placed on the specific risk zones while balancing out the potential for over-fitting the particular risks for a given run. In an exemplary simulation implementation an exemplary setting can be ZAP=0.75.

Since large and/or rapid changes in basal profile present problem both clinically (see document (see document "[12]" Laimer et al) and in terms of human factors—subjects may be uncomfortable with large changes—this raw new basal profile should be "leveled" so that large jumps and excessive variance in the profile are mitigated. The mechanisms of this leveling should included penalties for excessive jumps and rapid changes in magnitude throughout the day of the new basal profile, as well as caps on the deviance allowed from the previous iteration of the basal profile. After applying a leveling technique to the raw $B^*_{new}$ profile an implementable basal profile which is adjusted for hypoglycemic risk $B_{new}$ is obtained.

If there is no present hypoglycemic risk zoneband there are actionable zones of hyperglycemic risk then we can apply a mirror image of the above algorithm in order to adjust to profile to account for this. In essence then:

$$\text{Zone}^*_{HyperRisk} = \{t | I_{Percentile_{low}(t)} > B(t)\} \cap \text{Zone}_{HyperRisk},$$

and $$\alpha = \frac{Total_{above} - Total_{below}}{\int_{Zone^*_{HyperRisks}} B(t)dt},$$

thus, $$B^*_{new}(t) = B(t) + \alpha \cdot \delta_{Zone^*_{HyperRisks}}(t).$$

Again, a leveling procedure is applied to obtain $B_{new}(t)$—an implementable adaptation of the basal profile.

In an exemplary embodiment, the insulin dosage can be administered using an insulin dispensing valve that is controlled by the processor 102 to administer insulin in accordance with the updated basal rate set point. In an exemplary embodiment, the insulin dispensing valve has a retractable needle cannula and can be attached to the insulin device. The processor 102 can control the insulin delivered by the insulin dispensing valve to provide an optimal amount of insulin.

In order to demonstrate the proposed basal adaptation algorithm, an in silico trial was conducted using the one hundred adult subject in the FDA approved UVA/Padova Type 1 diabetes simulator as described in (see document "[13]" Dalla). The subjects underwent three simulated weeks under closed loop control using the Harvard zone model predictive controller (ZMPC) described in (see document "[14]" Gondhalekar). The experimental protocol consisted of 2-3 daily meals varying in timing, number, and carbohydrate composition throughout the week. The basal adaptation routine was applied in a "run-to-run" framework, with iterative adaptations of the profile occurring at the end of each week long run. The final profile resulting from this process and the original heuristic profile were then compared. Details of the experimental design and corresponding results are presented in this section.

Each of the 100 adult subjects in the UVA/Padova type 1 diabetes simulator were run twice through three weeks of closed loop control operating under an artificial pancreas using the zone model predictive control (ZMPC) algorithm described in "[14]" Gondhalekar et al. First the subjects underwent control using an unadapted profile derived from a standard clinical heuristic constant basal profile given by the assumption that the total insulin needed is roughly 0.6·BW where BW is the subject's body weight in kilograms, and that half of the total insulin delivered should be accounted for in the basal profile. Thus B(t)=0.3 (·BW)/288 was the baseline basal profile rate. Multiples of this baseline profile by a factor of 0.8, 1.2, and 1.4 as well as the profile itself were tested to see how the algorithm performed under varying possible initial basal rates.

Subjects consumed 2-3 pure carbohydrate meals per day of varying sizes: Breakfast was given—according to a normal random variable and written in terms of mean time delivered plus/minus standard deviation—at 07:15±01:00 each day, and, if delivered, consisted of 0.75±0.05·BW (in kg) grams of carbohydrates (again normal written as mean±standard deviation). Similarly, if lunch occurred it appeared at 12:30±01:00 and consisted of 0.9±0.05·BW (in kg) grams of carbohydrates, while dinner occurred at 19:00±01:00 and consisted of 1.0±0.2·BW (in kg) carbohydrates. To account for further potential variability in subjects' meal behaviors, on each day there was a one in five chance of a meal being skipped, and if this occurred one of the two remaining meals was increased in carbohydrate content by 25%. 42 days of meal behavior were generated in this way and formed the basis of our trial scenario. Subjects' data were gathered for the first 3 weeks under the unadapted constant basal profile. Then this first 3 weeks was rerun with the adaptation procedure implemented, with updates in the basal profile occurring every week. The final profile (after week 3) of this process was then used for the remaining 3 weeks of closed loop control and was compared to the unadapted results from the first 3 weeks.

The mean blood glucose level, standard deviation of the blood glucose reading, low blood glucose risk index (LBGI), high blood glucose risk index (HBGI), combined blood glucose risk index (BGRI)—as computed in (see document "[15]" Kovatchev et al)—and average daily risk range (ADRR as described in (see document [16] Kovatchev et al), though applied to CGM data in a natural extension), as well as time spent hypoglycemic (blood glucose <70 mg/dl), hyperglycemic (blood glucose>180 mg/dl) and blood glucose in a "tight" well controlled range (within 90-140 mg/dl) were all assessed in both the control and the adapted treatment runs by a paired T-test to detect if there was a statistically significant change in the average. Raw Means as well as T-statistics and corresponding p-values are shown in Table 1 and discussed in the following section.

The results of the experiment indicate that the subjects performed unambiguously better under the adapted versus the initial profile when the initial profile is set to 80%, 100%, or 120% of the baseline heuristic constant profile. The results are also suggestive in that by starting at the 120% profile the adapted profile produced noticeably better ADRR, BGRI, mean blood glucose, time experiencing hyperglycemia (BG>180 mg/dl) and time "tight" (90 mg/dl<BG<140 mg/dl) values than when the algorithm is applied to the baseline of 100% itself. This is consistent with the fact that the algorithm itself is biased towards mitigating hypoglycemia, so that starting from a slightly higher than standard initial profile produces better overall results in closed loop control in many metrics (mean BG, HBGI, BGRI, time>180 mg/dl, time 90-140 mg/dl), and statistically does no worse results in the remaining metrics. Starting with the profile at 80% and 100% of the baseline heuristic fewer obvious gains were made: the LBGI for the 100% baseline showed statistically significant improvement at the p=0.05 threshold, while for the 80% initial heuristic profile showed a statistically significant reduction in time hyperglycemic (BG>180 mg/dl) with reductions in HBGI and BGRI barely missing the p=0.05 cutoff. The 140% initial baseline heuristic profile was the only group which showed a statistically significant trade-off, with reductions in time in hypoglycemic range, LBGI, and ADRR, but an increase in mean blood glucose level, along with an increase in HBGI that is close to statistical significance.

The proposed algorithm uses both the action of the underlying AP controller itself and the CGM data to offer a heuristic adjustment of the basal insulin delivery rate profile. The routine is agnostic to the mechanisms of the underlying controller itself, except insofar as it is assumed to deliver insulin at a rate determined relative to the basal profile parameter. The in silico study of the algorithm implemented on the 100 adult subjects in the UVa/Padova type 1 diabetes simulator using the Harvard designed zone model predictive (ZMPC) AP controller demonstrates that adaptation of the basal profile according to the proposed heuristic procedure leads to better glycemic outcomes in several metrics, without any trade-offs in terms of poorer performance in others, when a baseline heuristic profile or perturbation within 20% of the baseline heuristic profile is used.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is descried herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Figure 2B:
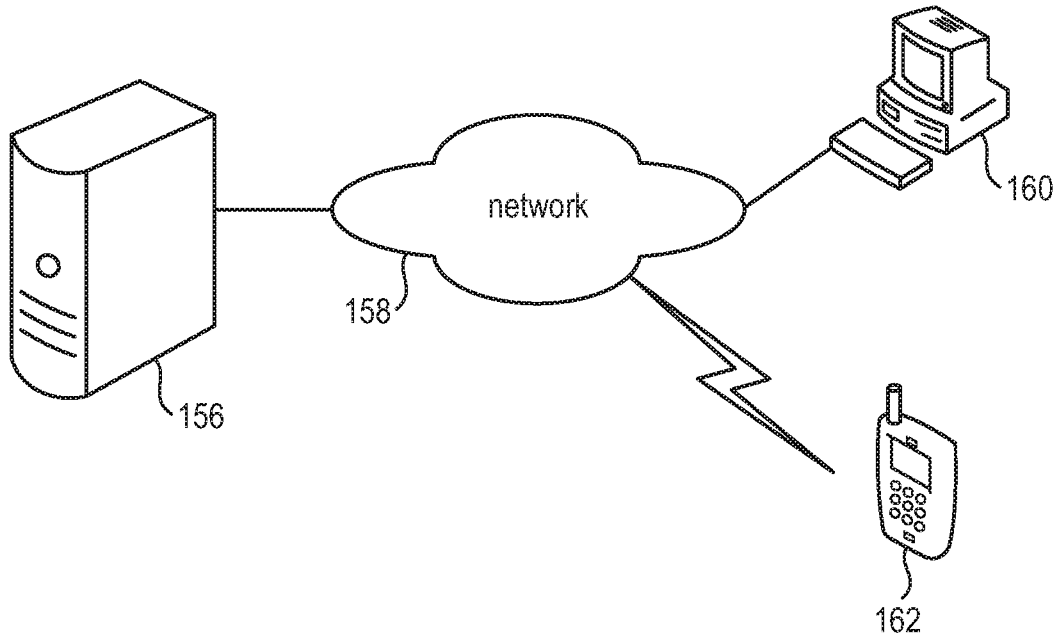
FIG. 2B illustrates a network system in which an embodiment of the disclosure can be implemented.

In addition to a stand-alone computing machine described herein, embodiments of the disclosure can also be implemented on a network system comprising a plurality of computing devices that are in communication with a networking means, such as a network with an infrastructure or an ad hoc network. The network connection can be wired connections or wireless connections. As a way of example, FIG. 2B illustrates a network system in which embodiments of the disclosure can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device (or glucose meter) and/or an insulin device. Any of the components shown or discussed with FIG. 2B may be multiple in number. The embodiments of the disclosure can be implemented in anyone of the devices of the system. For example, execution of the instructions or other desired processing can be performed on the same computing device that is anyone of 156, 160, and 162. Alternatively, an embodiment of the disclosure can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the disclosure. The processed, encoded or executed software can then be distributed to customers. The distribution can be in a form of storage media (e.g. disk) or electronic copy.

Figure 3:
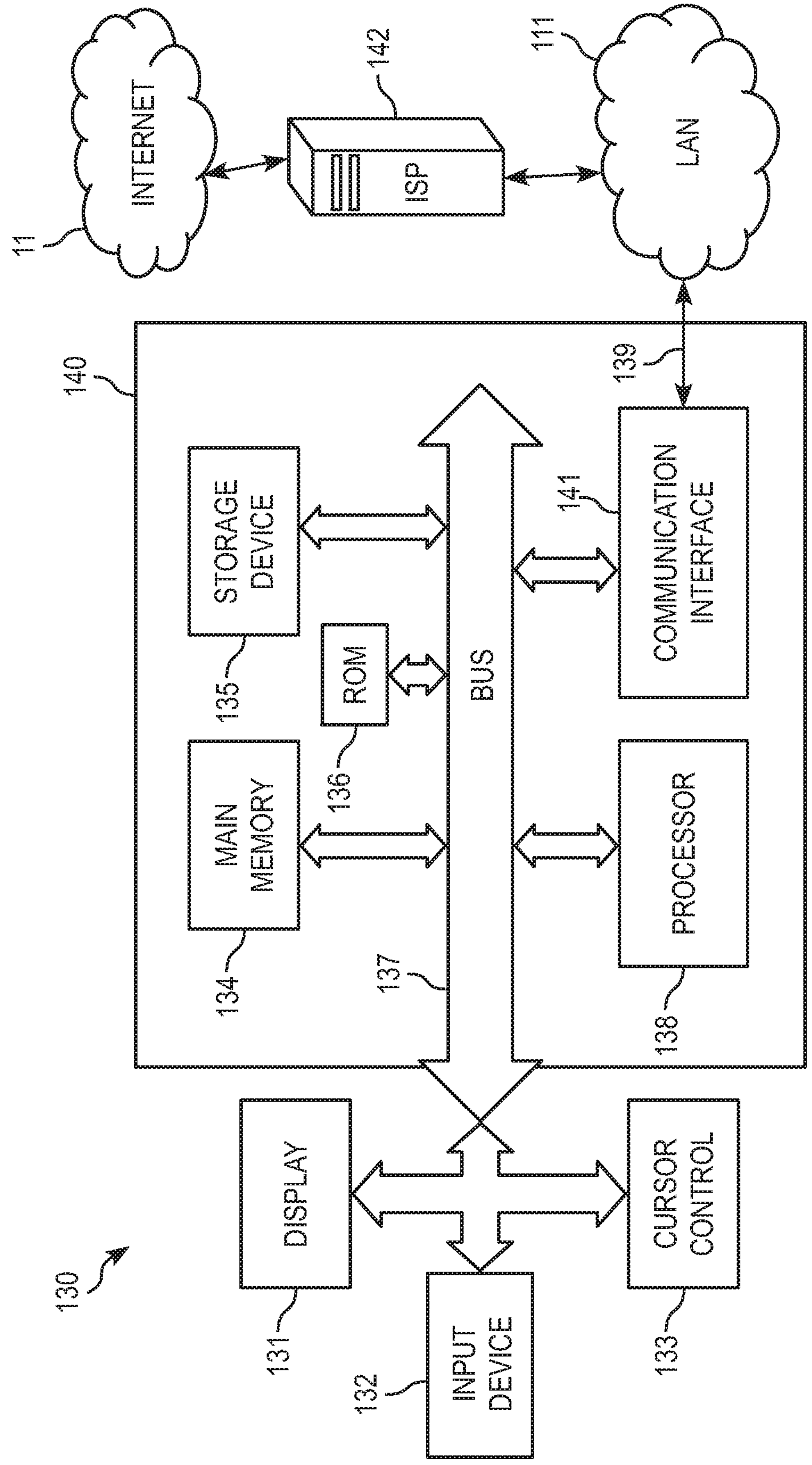
FIG. 3 is a block diagram that illustrates a system including a computer system and the associated Internet connection upon which an embodiment may be implemented.

FIG. 3 is a block diagram that illustrates a system 130 including a computer system 140 and the associated Internet 11 connection upon which an embodiment may be implemented. Such configuration is can be used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 3. The system 140 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices. Note that while FIG. 3 illustrates various components of a computer system, it is not intended to represent any particular architecture or manner of interconnecting the components; as such details are not germane to the present disclosure. It will also be appreciated that network computers, handheld computers, cell phones and other data processing systems which have fewer components or perhaps more components may also be used. The computer system of FIG. 3 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Computer system 140 can include an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device can have two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the disclosure are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (02-20-04), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 can provide data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of method and system for virtualization of virtual basal rates from planned and historical insulin delivery have been developed and disclosed herein; and may be implemented and utilized with the related processors, networks, computer systems, internet, and components and functions according to the schemes disclosed herein.

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a standalone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 410, input device 412 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

It should be appreciated that any of the components or modules referred to with regards to any of the present disclosure embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

It will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

What is claimed is:

1. A system configured to control an insulin dosage by adapting a basal rate profile, the system comprising:

a processor and associated computer memory device configured to receive glucose level measurement data and the basal rate profile, wherein the basal rate profile includes a basal rate set point that corresponds to an insulin delivery reference basal rate at which an amount of glucose present in blood of a patient tends to stabilize, and wherein the basal rate profile is stored in the computer memory device, the processor configured to:

update the basal rate set point for a time period t based on:

an assessment of at least one of a risk of hyperglycemia or a risk of hypoglycemia, the assessment performed on glucose level measurement data corresponding to a time period T, wherein T is a past time period, and t is a current or future time period corresponding to T;

data corresponding to insulin infusions delivered to the patient during the time period T to mitigate glycemic risk;

a minimum length of time constituting at least one of an addressable hyperglycemia risk zone of an addressable hypoglycemia risk zone; and a zone attribution parameter associated with the at least one of the addressable hyperglycemia risk zone or the addressable hypoglycemia risk zone, wherein the zone attribution parameter weights adjustments to the basal rate set point toward the at least one of the addressable hyperglycemia risk zone or the addressable hypoglycemia risk zone; and transmit a control signal configured to cause an insulin dispensing device to administer insulin in accordance with the updated basal rate set point.

2. The system of claim 1, wherein the processor is configured to:

determine the risk of hyperglycemia by measuring a first moving average of a high blood glucose risk function for a plurality of first time periods and computing an average of the measured first moving average; and determine the risk of hypoglycemia by measuring a second moving average of a low blood glucose risk function for the plurality of first time periods and computing an average of the measured second moving average.

3. The system of claim 2, wherein the processor is configured to determine the risk of hyperglycemia and the risk of hypoglycemia during a same time period, and counterpoise the risk of hyperglycemia and the risk of hypoglycemia by updating the basal rate set point.

4. The system of claim 2, wherein the processor is configured to mitigate the risk of hypoglycemia by updating the basal rate set point when both the risk of hyperglycemia and the risk of hypoglycemia are determined.

5. The system of claim 4, wherein the processor is configured to, after the risk of hypoglycemia is mitigated, mitigate the risk of hyperglycemia by updating the basal rate set point.

6. The system of claim 1, wherein the processor is configured to receive the glucose level measurement data from an artificial pancreas.

7. The system of claim 1, wherein the processor is configured to receive the glucose level measurement data by a manual input.

8. The system of claim 1, comprising the insulin dispensing device.

9. The system of claim 1, comprising a sensor configured to generate the glucose level measurement data and/or detect an update to the glucose level measurement data over time.

10. The system of claim 1, comprising:

an insulin device including:

the insulin dispensing device; and a sensor configured to generate the glucose level measurement data and/or detect an update to the glucose level measurement data over time.

11. The system of claim 1, wherein the assessment performed on the glucose level measurement data corresponding to the time period T involves assessing historical glucose level measurement data.

12. A computer-implemented method to control an insulin dosage by adapting a basal rate profile, the method comprising:

receiving glucose level measurement data and the basal rate profile, wherein the basal rate profile includes a basal rate set point that corresponds to an insulin delivery reference basal rate at which an amount of glucose present in blood of a patient tends to stabilize, and wherein the basal rate profile is stored in a computer memory;

updating the basal rate set point for a time period t based on:

an assessment of at least one of a risk of hyperglycemia or a risk of hypoglycemia, the assessment performed on glucose level measurement data corresponding to a time period T, wherein T is a past time period, and t is a current or future time period corresponding to T;

data corresponding to insulin infusions delivered to the patient during the time period T to mitigate glycemic risk;

a minimum length of time constituting at least one of an addressable hyperglycemia risk zone or an addressable hypoglycemia risk zone; and a zone attribution parameter associated with the at least one of the addressable hyperglycemia risk zone or the addressable hypoglycemia risk zone, wherein the zone attribution parameter weights adjustments to the basal rate set point toward the at least one of the addressable hyperglycemia risk zone or the addressable hypoglycemia risk zone; and transmitting a control signal that will cause an insulin dispensing device to administer insulin in accordance with the updated basal rate set point.

13. The method of claim 12, wherein the assessment performed on the glucose level measurement data corresponding to the time period T involves assessing historical glucose level measurement data.

14. A non-transitory computer readable recording medium encoded with a computer program comprising program instructions for causing a system to control an insulin dosage by adapting a basal rate profile, the computer program causing the system to:

receive glucose level measurement data and the basal rate profile, wherein the basal rate profile includes a basal rate set point that corresponds to an insulin delivery reference basal rate at which an amount of glucose present in blood of a patient tends to stabilize, and wherein the basal rate profile is stored in a computer memory;

update the basal rate set point for a time period t based on:

an assessment of at least one of a risk of hyperglycemia or a risk of hypoglycemia, the assessment performed on glucose level measurement data corresponding to a time period T, wherein T is a past time period, and t is a current or future time period corresponding to T;

data corresponding to insulin infusions delivered to the patient during the time period T to mitigate glycemic risk;

a minimum length of time constituting at least one of an addressable hyperglycemia risk zone or an addressable hypoglycemia risk zone; and a zone attribution parameter associated with the at least one of the addressable hyperglycemia risk zone or the addressable hypoglycemia risk zone, wherein the zone attribution parameter weights adjustments to the basal rate set point toward the at least one of the addressable hyperglycemia risk zone or the addressable hypoglycemia risk zone; and transmit a control signal that will cause an insulin dispensing device to administer insulin in accordance with the updated basal rate set point.

15. The non-transitory computer readable recording medium of claim 14, wherein the assessment performed on the glucose level measurement data corresponding to the time period T involves assessing historical glucose level measurement data.

* * * * *